United States Patent [19]

Bright et al.

[11] 4,397,757

[45] Aug. 9, 1983

[54] BLEACHING COMPOSITIONS HAVING QUARTERNARY AMMONIUM ACTIVATORS

[75] Inventors: Samuel C. Bright; Dennis Postlethwaite, both of Wirral, England

[73] Assignee: Lever Brothers Company, New York, N.Y.

[21] Appl. No.: 216,108

[22] Filed: Dec. 15, 1980

Related U.S. Application Data

[60] Division of Ser. No. 95,114, Nov. 16, 1979, abandoned, which is a continuation of Ser. No. 887,710, Mar. 17, 1978, abandoned, which is a continuation of Ser. No. 256,522, May 24, 1972, abandoned.

[51] Int. Cl.³ .................... C11D 3/395; D06L 3/06; C11D 7/54; C07C 101/02
[52] U.S. Cl. .................... 252/186.41; 252/95; 8/111; 252/186.29; 560/38
[58] Field of Search .................... 252/186, 95, 186.29, 252/186.41; 8/111; 560/38

[56] References Cited

U.S. PATENT DOCUMENTS

| | | | |
|---|---|---|---|
| 2,367,878 | 1/1945 | Lee | 560/38 |
| 2,727,923 | 12/1955 | Husted | 252/186 |
| 3,177,148 | 4/1965 | Bright et al. | 252/99 |

FOREIGN PATENT DOCUMENTS 7601512  2/1976  Netherlands ............ 252/186

*Primary Examiner*—Henry R. Jiles
*Assistant Examiner*—Robert C. Whittenbaugh
*Attorney, Agent, or Firm*—Milton L. Honig; James J. Farrell

[57] ABSTRACT

In a hydrogen peroxide bleaching system it is known to use an activator which forms a peracid bleaching species; specific esters have been proposed previously as activators. The present invention defines esters having a substantive moeity which provides improved bleaching by giving peracid generation at or near the substrate surface.

15 Claims, No Drawings

BLEACHING COMPOSITIONS HAVING QUARTERNARY AMMONIUM ACTIVATORS

This application is a divisional of application Ser. No. 95,144, filed Nov. 16, 1979, now abandoned, which in turn is a continuation of application Ser. No. 877,710, filed Mar. 17, 1978, now abandoned, which in turn is a continuation of application Ser. No. 256,522, filed May 24, 1972, now abandoned.

This invention relates to novel chemical compounds of use in bleach systems. The bleach systems of the invention may be used in combination with a detergent active system.

It is known to use active oxygen-releasing materials in bleaching systems, examples of these materials are hydrogen peroxide and inorganic "per-salts" such as percarbonate, perborate, persilicates and perphosphates. The term "per-salt" is used herein to mean a salt which releases hydrogen peroxide is aqueous solution. The materials listed above are not true per-salts in the strict chemical sense but are believed to contain hydrogen peroxide of crystallisation, which is liberated in aqueous solution. "Per-salts" are included in many detergent compositions to provide fabric bleaching during the washing procedure. Perborates are the most widely used per-salt. The bleaching efficiency of these per-salts decreases with reduction in the wash temperature and it has been proposed to introduce into the detergent composition an activator which reacts with the per-salt and sustains bleaching efficiency at lower temperatures. Materials which may be added to per-salt containing compositions in order to sustain the bleaching efficiency at lower temperatures will be referred to herein as bleach activators. These materials are believed to react with the hydrogen peroxide released by the per-salts, thereby forming bleaching agents which are more effective than hydrogen peroxide, particularly at low temperature. Examples of activators are esters as disclosed in UK Patent Specification No. 836988.

The novel chemical compounds of the present invention have properties which allow them to be used as bleach activators in combination with hydrogen peroxide or a per-salt as well as properties which cause the activator and intermediate species to be substantive to surfaces, for example those of fabrics. The term substantive is used to define a material which is preferentially adsorbed on a surface from a solution. In the present invention, this additional property of the activator can lead to further enhancement of the bleaching effect, particularly at low temperatures. Broadly, the invention proposes bleach activators, the molecule of which contains both a fabric substantive structure and a per-acid generating structure.

The present invention provides novel chemical compounds of the formula:

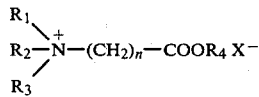

wherein n is 3 or more. The upper limit is determined by the utilisable solubility of the molecule and is about 25.

The total number of carbon atoms on the quaternary atom will be, at most, about 28.

$R_1$ is alkyl or substituted (for example by hydroxy) alkyl (having from 1 to 20 carbon atoms) or aryl, or alkaryl, or substituted aryl or polyoxyalkylene group, eg polyoxyethylene.

$R_2$, $R_3$ are each lower alkyl or hydroxyalkyl or two or more of $R_1$, $R_2$ $R_3$ are members of a nitrogen-containing heterocyclic ring system, for example pyridine, morpholine, pyrolidine, which may be substituted.

$R_4$ is phenyl or substituted phenyl.

X is chlorine or bromine.

The methylene chain may be branched.

A lower alkyl group is one with from one to four carbon atoms.

A detergent formulation containing a bleach system consisting of an active oxygen releasing material and a novel compound of the invention will also contain detergent-active materials, detergency builders and other known ingredients of such formulations.

The detergent-active will be selected from any of the known materials and may be, for example, of the anionic, cationic, nonionic or amphoteric classes. Examples are alkyl benzene sulphonates, alcohol sulphates, alcohol ether sulphates, sulphonated olefins, alkane sulphonates and ethoxylated alcohols. Other examples are listed by Schwartz, Perry and Berch in Volume 2 of their book "Surface Active Agents and Detergents" (1958). The only necessary limitation to be placed on detergent actives is that they do not precipitate insoluble salts with the esters of the invention. Such a precipitation will occur between anionic actives and those esters having a relatively large number of carbon atoms attached to the quaternary nitrogen atom. When an anionic active is used the preferred range of esters has n in the range from 3 to 10 and a relatively short alkyl chain in the group $R_1$. The compatibility of any active with the esters of the invention can be tested in a simple manner before their use in a formulation.

The formulation may also contain detergency builders, for example phosphate materials, for example tripolyphosphate and orthophosphate salts, nitrilotriacetic acid, carbonate salts and silicates. Other inorganic salts, for example sodium sulphate may also be present. The optional ingredients of a formulation, ie antiredeposition agents, for example sodium carboxymethyl cellulose, fluorescers and enzymes, will be present. The esters of the present invention may also be used with non-substantive activators, for example phthalic anhydride and tetraacetyl ethylene diamine.

The molecular ratio of activator to oxygen releasing compound is preferably in the range from 0.5 to 1.5 and as will be appreciated the optimum efficiency is realized when the two materials are present in stoichiometric amounts.

When the compounds of the invention and the intermediates generated by reaction with hydrogen peroxide contact a fabric surface they become adsorbed thereon. Thus a localised action is obtained and the bleaching efficiency obtained from these bleach activators is exceptionally high. It will be appreciated that this increased efficiency is obtained because the bleaching species are localised on the fabric surface instead of being dispersed throughout the aqueous phase, as with a non-substantive system.

The compounds of the invention may be prepared broadly as follows:

An η-ω halo carboxylic acid (1 mole), in which the number of carbon atoms is greater than three, is refluxed with excess thionyl chloride (2 moles) to form the acid chloride. This latter is purified by distillation, preferably at reduced pressure and then reacted (1 mole) with excess phenol (2 moles) to form the α-ω halo phenyl ester, which is purified by distillation and/or recrystallisation. The quaternary ester is then obtained from the reaction between the above ester (1 mole) and an excess of a tertiary amine (2–10 moles), using the excess amine as the solvent for the reaction. At this stage, the reaction medium usually becomes solid and the quaternary ammonium phenyl ester is isolated from it in a pure state by copious washing of the mass with organic solvent (eg diethyl ether) followed by recrystallisation.

In some instances, depending upon the availability of the staring materials (Principally, the α-ω halo carboxylic acid) it is necessary to change the halide counter-ion of the quaternised ester in order to enhance the stability of the peracid generated in use. This is easily accomplished by using an anionic ion-exchange resin in the chloride form. A concentrated solution of the ester is run down a column containing the resin and the final ester, containing the new counter-ion, isolated from the eluate by precipitation with an organic solvent (eg diethyl ether).

The general procedure can be represented conventionally by the following chemical equations:

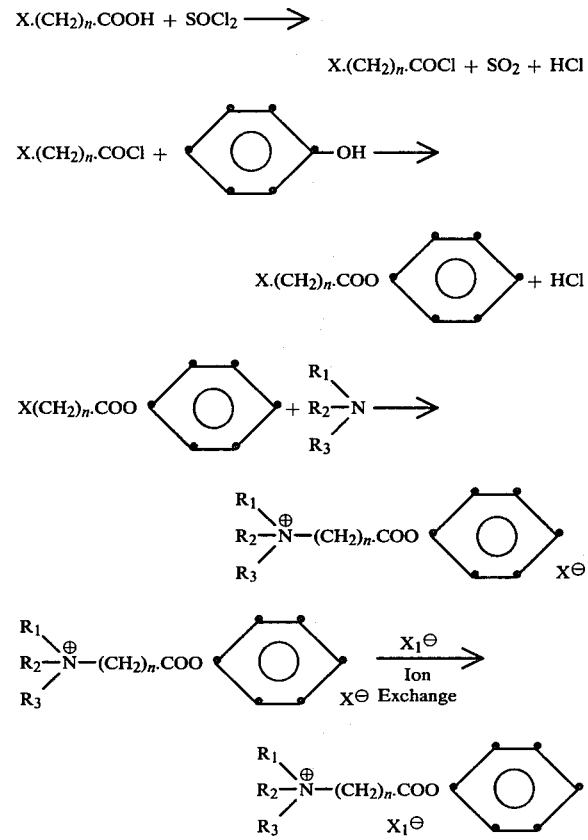

Specific Preparation I

N N Dimethyl, N Octyl N-10Carbophenoxy Decyl Ammonium Bromide (I)

This compound was prepared in three stages:
1. 55 g (0.20 moles) of recrystallised 11-bromo undecanoic acid were refluxed with 48 g (0.4 moles) of thionyl chloride for 3 hours. Excess thionyl chloride was then removed by vacuum distillation at 10–14 mm Hg pressure. The crude acid chloride remaining was distilled under higher vacuum (0.1 mm Hg) to give 50 g (0.18 moles) of pure 11-bromo undecanoyl chloride.

2. 14.2 g (0.05 moles) of 11-bromo undecanoyl chloride and 9.4 g (0.1 mole) of phenol were heated at 100° C. on a steam bath until evolution of gaseous hydrogen chloride had ceased. Excess phenol was then distilled off at 10–14 mm Hg pressure. The crude ester remaining was finally vacuum distilled at ~1 mm Hg pressure to give 14 g (0.04 moles) of pure phenyl 11-bromo undecanoate as a clear liquid.

3. 3.5 g (0.01 moles) of phenyl 11-bromo undecanoate were warmed with 15 ml (0.1 mole) octyl dimethyl amine (ie in excess), on a steam bath at 100° C. for 4 hours and under anhydrous conditions. The mixture was then allowed to cool and stand overnight, following which period a white solid had formed. This was slurried in diethyl ether and the suspended solid, crude N N dimethy N Octyl N-10 Carbophenoxy Decyl Ammonium Bromide (I) filtered off. The filter cake obtained was washed several times with diethyl ether and was finally recrystallised from a diethyl ether:acetone (in a 10:1 vol:vol:ratio) solvent, to yield 3.9 g (0.008 moles) of pure N N Dimethyl N Octyl N-10 Carbophenoxy Decyl Ammonium Bromide (I) as a white solid.

Specific Preparation II

N N Dimethyl N Octyl N-10 Carbophenoxy Decyl Ammonium Chloride (II)

2.0 g (0.004 moles) of N N Dimethyl N Octyl N-10 Carbophenoxy Decyl Ammonium Bromide (I) were dissolved in 100 ml distilled water. The resultant solution was eluted down an ion-exchange column containing beads of Amberlite IRA-400 ion-exchange resin in the chloride (Cl$^\ominus$) form. (This resin has been generated in the chloride form by soaking in strong brine solution beforehand.) Elution was continued until no halide, as detected by silver nitrate solution, was present in the eluate. The water in the latter was then removed by azeotroping it with copious aounts of initially acetone and finally diethyl ether using a rotary film evaporator. Eventually 1.5 g (0.003 moles) of white N N Dimethyl N Octyl N-10 Carbophenoxy Decyl Ammonium Chloride (II) were obtained.

Table I lists compounds of the invention as examples of the class to which the invention relates.

TABLE I

| n | $R_1$ | $R_2$ | $R_3$ | $R_4$ | R |
|---|---|---|---|---|---|
| 10 | $C_8H_{17}$ | $CH_3$ | $CH_3$ | $C_6H_5$ | Br |
| 10 | $C_8H_{17}$ | $CH_3$ | $CH_3$ | $C_6H_5$ | Cl |
| 10 | $C_{16}H_{33}$ | $CH_3$ | $CH_3$ | $C_6H_5$ | Br |
| 10 | $C_2H_5$ | $C_2H_5$ | $C_2H_5$ | $C_6H_5$ | Br |
| 10 | $C_2H_4OH$ | $C_2H_5$ | $C_2H_5$ | $C_6H_5$ | Br |
| 10 | $C_2H_4OH$ | $C_2H_4OH$ | $C_2H_4OH$ | $C_6H_5$ | Br |
| 10 | $C_6H_5$ | $CH_3$ | $CH_3$ | $C_6H_5$ | Br |
| 10 | 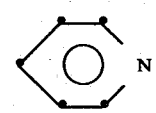 | | | $C_6H_5$ | Br |

TABLE I-continued

| n | $R_1$ | $R_2$ | $R_3$ | $R_4$ | R |
|---|-------|-------|-------|-------|---|
| 10 | | pyridinyl | | $C_6H_5$ | Cl |
| 10 | | 3,5-dimethylpyridinyl | | $C_6H_5$ | Br |
| 3 | $C_8H_{17}$ | $CH_3$ | $CH_3$ | $C_6H_5$ | Cl |

Examples illustrating the use of compounds of the invention will now be given.

EXAMPLE I

Bleaching tests were performed on tea stained cotton at temperatures of 25°, 40° and 60° C. using a liquor:-cloth ratio of 15:1. In the 25° C. tests an additional test using sodium hypochlorite equivalent to the available oxygen in the other tests was performed. The tests studied:

(i) the bleaching efficiency with concentration over a 15 minute bleach, and (ii) the bleaching efficiency with time using a sodium perborate concentration of 0.032 wt %. The results were performed using three compounds of the invention.

1. N octyl N N dimethyl N-10 carbophenoxy decyl ammonium chloride (ODC)
2. The bromide salt of 1 (ODB)
3. N-10 carbophenoxy decyl pyridinium bromide (PDB)

The known compounds sodium acetoxy benzene sulphonate (SABS) and tetra acetyl ethylene diamine (TAED) were used as standards.

1:1 molar ratios of activator:perborate were used except for TAED when the ratio was 0.5:1 and the bleaching efficiency determined using an Elrepho reflectometer (filters 460 nm and FL 46 in combination). The reproducibility of the experiments was good and the error estimated at ±5%, Tables II and III show the results, the bleaching efficiencies were determined using the average of four runs.

TABLE II

Results of Concentration Experiments (15 min Bleach)

| SYSTEM | | BLEACHING EFFICIENCIES PERBORATE CONCENTRATION (at %) | | | | | | | |
|---|---|---|---|---|---|---|---|---|---|
| TEMP | ACTIVATOR | 0.011 | 0.021 | 0.032 | 0.043 | 0.064 | 0.075 | 0.080 | 0.100 |
| 25° C. | None | 0.2 | — | 1.4 | — | 0.6 | 0.4 | — | 0.4 |
| " | TAKD | 1.0 | — | 5.1 | — | 18.1 | 21.7 | — | 27.8 |
| " | SABS | 6.7 | — | 9.8 | — | 12.8 | 14.2 | — | 16.7 |
| " | ODB | 1.6 | — | 2.0 | — | 34.8 | 36.8 | — | 33.7 |
| " | ODC | 1.2 | — | 14.6 | — | 48.3 | 45.9 | — | 32.7 |
| " | PDB | 6.3 | — | 15.7 | — | 21.7 | 24.2 | — | 27.0 |
| " | NaOCl (used alone) | 11.0 | — | 19.7 | — | 37.4 | 40.4 | — | 51.8 |
| 40° C. | None | 5.5 | — | 8.9 | — | 8.5 | — | — | 8.5 |
| 22.0 | TAED | 8.9 | — | 13.6 | — | 19.1 | — | — | |
| " | SABS | 12.0 | — | 18.5 | — | 13.8 | — | — | 31.7 |
| " | ODB | 5.7 | — | 20.1 | — | 21.7 | — | — | 15.0 |
| " | ODC | 7.5 | — | 21.5 | — | 44.5 | — | — | 26.0 |
| " | PDB | 10.2 | — | 22.2 | — | 30.1 | — | — | 29.1 |
| 60° C. | None | 0.2 | 8.1 | 8.7 | 8.7 | 8.7 | — | 9.3 | 9.8 |
| " | TAED | 4.1 | 15.9 | 18.3 | 20.1 | 23.4 | — | 28.9 | 33.5 |
| " | SABS | 7.1 | 17.9 | 21.1 | 23.0 | 27.0 | — | 32.3 | 39.4 |
| " | ODB | 4.5 | 11.4 | 13.4 | 14.6 | 15.4 | — | 16.7 | 17.5 |
| " | ODC | 2.4 | 21.1 | 27.6 | 31.1 | 38.8 | — | 40.2 | 10.7 |
| " | PDB | 8.7 | 14.6 | 18.3 | 20.1 | 22.8 | — | 23.4 | 21.0 |

The bleaching efficiency (BE) is determined by the formula:

$$BE = \frac{R}{Rm} \times 100 \text{ where } R = Ra - Rb$$

Ra is reflectance of test piece after treatment.
Rb is reflectance of test piece before treatment.
Rm is maximum possible increase in reflectance—formed by using clean, desized cotton cloth.

TABLE III

Results of Time Experiments (0.032 wt % Perborate)

| SYSTEM | | BLEACHING EFFICIENCIES TIME (MIN) | | | | | | | |
|---|---|---|---|---|---|---|---|---|---|
| TEMP | ACTIVATOR | 1 | 2 | 5 | 7 | 10 | 15 | 60 | 180 |
| 25° C. | TAED | — | — | — | — | — | 5.1 | 23.0 | 18.8 |
| " | SABS | — | — | — | — | — | 9.8 | 28.5 | 18.7 |
| " | OO | — | — | — | — | — | 2.0 | 15.0 | 11.0 |
| " | OOC | — | — | — | — | — | 14.6 | 33.7 | 25.5 |
| " | PDB | — | — | — | — | — | 15.7 | 39.4 | 20.4 |
| 40° C. | TAED | 3.0 | 4.1 | 9.6 | 10.0 | 12.6 | 13.6 | — | — |
| " | SABS | 3.0 | 8.1 | 13.0 | 15.2 | 16.9 | 18.5 | — | — |
| " | OOC | 5.5 | 13.2 | 17.3 | 18.3 | 20.3 | 21.5 | — | — |
| 60° C. | TAED | 3.0 | 5.7 | 12.8 | 14.8 | 17.9 | 18.3 | — | — |
| " | SABS | 4.9 | 7.7 | 14.6 | 18.3 | 19.7 | 21.1 | — | — |

TABLE III-continued

Results of Time Experiments (0.032 wt % Perborate)

| SYSTEM | | BLEACHING EFFICIENCIES TIME (MIN) | | | | | | |
|---|---|---|---|---|---|---|---|---|
| TEMP | ACTIVATOR | 1 | 2 | 5 | 7 | 10 | 15 | 60 | 180 |
| " | ODB | 6.9 | 10.8 | 16.5 | 16.5 | 17.1 | 13.4 | — | — |
| " | OOC | 8.7 | 15.7 | 21.1 | 22.8 | 26.0 | 27.6 | — | — |
| " | PDB | 4.9 | 8.9 | 8.5 | 13.4 | 17.5 | 18.3 | — | — |

EXAMPLE II

This Example demonstrated the substantivity of the activators by first soaking a tea stained cotton test piece in a solution of the activator and then immersing it in a sodium perborate solution.

50 ml of a solution of the activator was prepared, the amount of activator used being equivalent to 50 ml of either 0.032 wt % or 0.064 wt % perborate. The test cloth (12"×3") was then soaked in this solution for a known time at the required temperature, (generally ambient). It was then removed, squeezed dry and washed in perborate (0.032 wt %) pyrophosphate solution at 60° C. and the bleaching efficiencies determined in the normal manner. It was observed in these tests that the uptake of liquid from the solution by the test cloth was ~6.0 ml. The results are given in Table IV.

TABLE IV

| ACTIVATOR | BLEACHING EFFICIENCY | | | | | |
|---|---|---|---|---|---|---|
| ACTIVATOR CONC. | $2.0 \times 10^{-3}$M | | | | $4.0 \times 10^{-3}$M | |
| SOAK TIME (MIN) | 2 | 60 | 180 | 60* | 5 | 60++ |
| None | 8.7 | 8.1 | 6.9 | 8.1 | 7.7 | 13.0 |
| TAED | 10.4 | 10.2 | 11.0 | 9.3 | 12.6 | 17.7 |
| SABS | — | 14.2 | 8.9 | 10.8 | — | 18.9 |
| ODC | 13.6 | 20.7 | 13.8 | 19.5 | 15.2 | 23.2 |
| ODB | — | 22.6 | 16.9 | 20.5 | — | 32.5 |
| PDB | — | 22.2 | 15.7 | 15.9 | — | 20.3 |

*= Soaked at 60° C.
++ = Washed in 0.064 wt % Perborate
A further attribute of those compounds is their anti-butanol properties.

The anti-bacterial properties, as the Minimum Inhibitory Concentration (MIC), of ODC, ODB and PDB were determined and found to be:

| | MIC (ppm) | |
|---|---|---|
| | E. coli | Staph. Aureus |
| ODC | 200/150 | 10/5 |
| ODB | 30/10 | 3/1 |
| PDB | 10/5 | 3/1 |

What is claimed is:

1. A bleaching formulation consisting essentially of a hydrogen-peroxide releasing material and a chemical compound of the formula

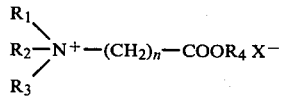

wherein n is 3 to about 25;
R$_1$ is a radical selected from the group consisting of alkyl, alkaryl, aryl, hydroxyalkyl and polyoxyalkylene;
R$_2$ and R$_3$ are each a radical selected from the group lower alkyl and hydroxyalkyl;
or two or more of R$_1$, R$_2$, or R$_3$ together form an alkyl substituted or unsubstituted nitrogen-containing heterocyclic ring system selected from the group consisting of pyridine, morpholine, and pyrrolidine;
R$_4$ is a phenyl group;
X is selected from the group of chlorine and bromine; and the total number of carbon atoms on the quaternary atom are less than about 28.

2. The bleaching formulation of claim 1 wherein the chemical compound is present in an amount of from about 0.5 to 1.5 moles per mole of hydrogen peroxide releasing material.

3. A method of bleaching fabric using the bleaching formulation of claim 1.

4. A washing formulation consisting essentially of the bleaching formulation of claim 1 in combination with a detergent active material.

5. A bleaching formulation according to claim 1 wherein the compound of formula I is N-Octyl NN-Dimethyl N-(10-Carbophenoxydecyl) Ammonium Bromide.

6. A bleaching formulation according to claim 1 wherein the compound of formula I is N-Octyl NN-Dimethyl N-(10-Carbophenoxydecyl) Ammonium Chloride.

7. A bleaching formulation according to claim 1 wherein the compound of formula I is N-Hexadecyl NN-Dimethyl N-(10-Carbophenoxydecyl) Ammonium Bromide.

8. A bleaching formulation according to claim 1 wherein the compound of formula I is NNN-Triethyl N-(10-Carbophenoxydecyl) Ammonium Bromide.

9. A bleaching formulation according to claim 1 wherein the compound of formula I is NN-Diethyl N-(2-Hydroxyethyl) N-(10-Carbophenoxydecyl) Ammonium Bromide.

10. A bleaching formulation according to claim 1 wherein the compound of formula I is NNN-Tri(2-Hydroxyethyl) N-(10-Carbophenoxydecyl) Ammonium Bromide.

11. A bleaching formulation according to claim 1 wherein the compound of formula I is N-Phenyl NN-Dimethyl N-(10-Carbophenoxydecyl) Ammonium Bromide.

12. A bleaching formulation according to claim 1 wherein the compound of formula I is N-(10-Carbophenoxydecyl) Pyridinium Bromide.

13. A bleaching formulation according to claim 1 wherein the compound of formula I is N-(10-Carbophenoxydecyl) Pyridinium Chloride.

14. A bleaching formulation according to claim 1 wherein the compound of formula I is N-(10-Carbophenoxydecyl) Collidinium Bromide.

15. A bleaching formulation according to claim 1 wherein the compound of formula I is N-Octyl NN-Dimethyl N-(3-Carbophenoxypropyl) Ammonium Chloride.

* * * * *